US012539358B2

(12) United States Patent
Rice et al.

(10) Patent No.: US 12,539,358 B2
(45) Date of Patent: Feb. 3, 2026

(54) SYSTEMS AND METHODS FOR SCHEDULING AND CONTROLLING WOUND THERAPY

(71) Applicant: Solventum Intellectual Properties Company, Maplewood, MN (US)

(72) Inventors: Justin Rice, San Antonio, TX (US); Christopher Allen Carroll, San Antonio, TX (US); Shannon C. Ingram, Bulverde, TX (US); Brett L. Moore, San Antonio, TX (US)

(73) Assignee: Solventum Intellectual Properties Company, Maplewood, MN (US)

( * ) Notice: Subject to any disclaimer, the term of this patent is extended or adjusted under 35 U.S.C. 154(b) by 145 days.

(21) Appl. No.: 16/562,107

(22) Filed: Sep. 5, 2019

(65) Prior Publication Data

US 2020/0069183 A1 Mar. 5, 2020

Related U.S. Application Data

(60) Provisional application No. 62/727,403, filed on Sep. 5, 2018.

(51) Int. Cl.
*A61M 1/00* (2006.01)
*A61B 5/00* (2006.01)
(Continued)

(52) U.S. Cl.
CPC ............. *A61M 1/92* (2021.05); *A61B 5/0002* (2013.01); *A61F 13/05* (2024.01); *A61M 1/732* (2021.05);
(Continued)

(58) Field of Classification Search
CPC ................ A61B 5/0002; A61M 1/732; A61M 2205/3584; A61M 1/85; A61M 1/74;
(Continued)

(56) References Cited

U.S. PATENT DOCUMENTS

| | | | |
|---|---|---|---|
| 1,355,846 | A | 10/1920 | Rannells |
| 2,547,758 | A | 4/1951 | Keeling |

(Continued)

FOREIGN PATENT DOCUMENTS

| | | | |
|---|---|---|---|
| AU | 550575 | B2 | 3/1986 |
| AU | 745271 | B2 | 3/2002 |

(Continued)

OTHER PUBLICATIONS

What is an Electronic Controller?, Trerice, http://www.cpinc.com/trerice/Control/control_43_44.pdf (Year: 2001).*

(Continued)

*Primary Examiner* — Rebecca E Eisenberg
*Assistant Examiner* — Alessandro R Del Priore

(57) ABSTRACT

Systems and methods for providing negative-pressure therapy with fluid instillation therapy and, more specifically, scheduling and controlling both the negative pressure therapy and the fluid instillation therapy are described. The method may comprise applying negative pressure to the dressing based on an initial therapy configuration, and monitoring negative pressure parameters associated with the application of negative pressure to the dressing to identify negative pressure alarm conditions. The method may further comprise applying instillation fluid to the dressing based on the initial therapy configuration, and monitoring instillation parameters associated with the application of instillation fluid to the dressing to identify instillation alarm conditions. Both may include modifying the initial therapy configuration to generate a modified therapy configuration in response to the negative pressure and instillation alarm conditions identified.

20 Claims, 5 Drawing Sheets

(51) Int. Cl.
*A61F 13/00* (2024.01)
*A61F 13/05* (2024.01)
*A61F 13/0246* (2024.01)

(52) U.S. Cl.
CPC ..... *A61M 1/96* (2021.05); *A61F 2013/00174* (2013.01); *A61F 2013/0094* (2013.01); *A61F 13/0253* (2013.01); *A61M 1/772* (2021.05); *A61M 2205/3584* (2013.01)

(58) Field of Classification Search
CPC ............ A61M 1/90; A61M 2205/6018; A61M 2205/6072; A61M 3/0258; A61M 2205/18; A61M 2205/15; A61M 2205/3331; A61M 2205/3382; A61M 2205/50; A61F 13/0216; A61F 13/0253; A61F 2013/00174; A61F 2013/0094; G16H 20/10; G16H 20/13; G16H 20/17; G16H 20/30; G16H 20/40; G16H 20/60; G16H 20/70; G16H 40/60
See application file for complete search history.

(56) References Cited

U.S. PATENT DOCUMENTS 2,632,443 A 3/1953 Lesher
2,682,873 A 7/1954 Evans et al.
2,910,763 A 11/1959 Lauterbach
2,969,057 A 1/1961 Simmons
3,066,672 A 12/1962 Crosby, Jr. et al.
3,367,332 A 2/1968 Groves
3,520,300 A 7/1970 Flower, Jr.
3,568,675 A 3/1971 Harvey
3,648,692 A 3/1972 Wheeler
3,682,180 A 8/1972 McFarlane
3,826,254 A 7/1974 Mellor
4,080,970 A 3/1978 Miller
4,096,853 A 6/1978 Weigand
4,139,004 A 2/1979 Gonzalez, Jr.
4,165,748 A 8/1979 Johnson
4,184,510 A 1/1980 Murry et al.
4,233,969 A 11/1980 Lock et al.
4,245,630 A 1/1981 Lloyd et al.
4,256,109 A 3/1981 Nichols
4,261,363 A 4/1981 Russo
4,275,721 A 6/1981 Olson
4,284,079 A 8/1981 Adair
4,297,995 A 11/1981 Golub
4,333,468 A 6/1982 Geist
4,373,519 A 2/1983 Errede et al.
4,382,441 A 5/1983 Svedman
4,392,853 A 7/1983 Muto
4,392,858 A 7/1983 George et al.
4,419,097 A 12/1983 Rowland
4,465,485 A 8/1984 Kashmer et al.
4,475,909 A 10/1984 Eisenberg
4,480,638 A 11/1984 Schmid
4,525,166 A 6/1985 Leclerc
4,525,374 A 6/1985 Vaillancourt
4,540,412 A 9/1985 Van Overloop
4,543,100 A 9/1985 Brodsky
4,548,202 A 10/1985 Duncan
4,551,139 A 11/1985 Plaas et al.
4,569,348 A 2/1986 Hasslinger
4,605,399 A 8/1986 Weston et al.
4,608,041 A 8/1986 Nielsen
4,640,688 A 2/1987 Hauser
4,655,754 A 4/1987 Richmond et al.
4,664,662 A 5/1987 Webster
4,710,165 A 12/1987 McNeil et al.
4,733,659 A 3/1988 Edenbaum et al.
4,743,232 A 5/1988 Kruger
4,758,220 A 7/1988 Sundblom et al.
4,787,888 A 11/1988 Fox
4,826,494 A 5/1989 Richmond et al.
4,838,883 A 6/1989 Matsuura
4,840,187 A 6/1989 Brazier
4,863,449 A 9/1989 Therriault et al.
4,872,450 A 10/1989 Austad
4,878,901 A 11/1989 Sachse
4,897,081 A 1/1990 Poirier et al.
4,906,233 A 3/1990 Moriuchi et al.
4,906,240 A 3/1990 Reed et al.
4,919,654 A 4/1990 Kalt
4,941,882 A 7/1990 Ward et al.
4,953,565 A 9/1990 Tachibana et al.
4,969,880 A 11/1990 Zamierowski
4,985,019 A 1/1991 Michelson
5,037,397 A 8/1991 Kalt et al.
5,086,170 A 2/1992 Luheshi et al.
5,092,858 A 3/1992 Benson et al.
5,100,396 A 3/1992 Zamierowski
5,134,994 A 8/1992 Say
5,149,331 A 9/1992 Ferdman et al.
5,167,613 A 12/1992 Karami et al.
5,176,663 A 1/1993 Svedman et al.
5,215,522 A 6/1993 Page et al.
5,232,453 A 8/1993 Plass et al.
5,261,893 A 11/1993 Zamierowski
5,278,100 A 1/1994 Doan et al.
5,279,550 A 1/1994 Habib et al.
5,298,015 A 3/1994 Komatsuzaki et al.
5,342,376 A 8/1994 Ruff
5,344,415 A 9/1994 DeBusk et al.
5,358,494 A 10/1994 Svedman
5,437,622 A 8/1995 Carion
5,437,651 A 8/1995 Todd et al.
5,527,293 A 6/1996 Zamierowski
5,549,584 A 8/1996 Gross
5,556,375 A 9/1996 Ewall
5,607,388 A 3/1997 Ewall
5,636,643 A 6/1997 Argenta et al.
5,645,081 A 7/1997 Argenta et al.
6,071,267 A 6/2000 Zamierowski
6,135,116 A 10/2000 Vogel et al.
6,241,747 B1 6/2001 Ruff
6,287,316 B1 9/2001 Agarwal et al.
6,345,623 B1 2/2002 Heaton et al.
6,488,643 B1 12/2002 Tumey et al.
6,493,568 B1 12/2002 Bell et al.
6,553,998 B2 4/2003 Heaton et al.
6,814,079 B2 11/2004 Heaton et al.
7,846,141 B2 12/2010 Weston
8,062,273 B2 11/2011 Weston
8,216,198 B2 7/2012 Heagle et al.
8,251,979 B2 8/2012 Malhi
8,257,327 B2 9/2012 Blott et al.
8,398,614 B2 3/2013 Blott et al.
8,449,509 B2 5/2013 Weston
8,529,548 B2 9/2013 Blott et al.
8,535,296 B2 9/2013 Blott et al.
8,551,060 B2 10/2013 Schuessler et al.
8,568,386 B2 10/2013 Malhi
8,679,081 B2 3/2014 Heagle et al.
8,834,451 B2 9/2014 Blott et al.
8,926,592 B2 1/2015 Blott et al.
8,974,428 B2 3/2015 Freedman et al.
9,017,302 B2 4/2015 Vitaris et al.
9,198,801 B2 12/2015 Weston
9,211,365 B2 12/2015 Weston
9,289,542 B2 3/2016 Blott et al.
2002/0077661 A1 6/2002 Saadat
2002/0115951 A1 8/2002 Norstrem et al.
2002/0120185 A1 8/2002 Johnson
2002/0143286 A1 10/2002 Tumey
2002/0198503 A1* 12/2002 Risk, Jr. ................ A61M 35/30 604/315
2007/0239078 A1* 10/2007 Jaeb ........................ A61N 7/00 601/2
2011/0190735 A1* 8/2011 Locke ................... F04B 45/047 604/543
2011/0264044 A1* 10/2011 Bartz .................... A61M 5/145 604/151

(56) References Cited

U.S. PATENT DOCUMENTS

| | | | | |
|---|---|---|---|---|
| 2013/0085462 A1* | 4/2013 | Nip | A61M 1/962 | 604/315 |
| 2013/0165821 A1* | 6/2013 | Freedman | A61F 13/0279 | 604/20 |
| 2013/0267920 A1* | 10/2013 | Nicolini | A61M 1/96 | 604/319 |
| 2013/0317837 A1* | 11/2013 | Ballantyne | A61M 1/3627 | 705/2 |
| 2014/0163491 A1 | 6/2014 | Schuessler et al. | | |
| 2014/0188076 A1* | 7/2014 | Kamen | F04B 1/26 | 604/154 |
| 2015/0080788 A1 | 3/2015 | Blott et al. | | |
| 2015/0290364 A1 | 10/2015 | Wall et al. | | |
| 2016/0015872 A1* | 1/2016 | Luckemeyer | A61M 3/0254 | 604/315 |
| 2016/0184497 A1* | 6/2016 | Phillips | G16H 40/63 | 604/318 |
| 2017/0151095 A1* | 6/2017 | Robinson | A61L 15/58 | |
| 2019/0269851 A1* | 9/2019 | Panotopoulos | A61M 1/772 | |
| 2019/0295718 A1* | 9/2019 | Lawhorn | A61M 1/96 | |
| 2020/0105393 A1* | 4/2020 | Keefe | A61M 5/315 | |
| 2020/0289347 A1* | 9/2020 | Gowans | A61M 1/916 | |
| 2021/0085853 A1* | 3/2021 | Chen | A61M 3/0208 | |

FOREIGN PATENT DOCUMENTS

| | | | | |
|---|---|---|---|---|
| AU | 755496 B2 | 12/2002 | | |
| CA | 2005436 A1 | 6/1990 | | |
| DE | 26 40 413 A1 | 3/1978 | | |
| DE | 43 06 478 A1 | 9/1994 | | |
| DE | 29 504 378 U1 | 9/1995 | | |
| EP | 0100148 A1 | 2/1984 | | |
| EP | 0117632 A2 | 9/1984 | | |
| EP | 0161865 A2 | 11/1985 | | |
| EP | 0358302 A2 | 3/1990 | | |
| EP | 1018967 A1 | 7/2000 | | |
| GB | 692578 A | 6/1953 | | |
| GB | 2195255 A | 4/1988 | | |
| GB | 2 197 789 A | 6/1988 | | |
| GB | 2 220 357 A | 1/1990 | | |
| GB | 2 235 877 A | 3/1991 | | |
| GB | 2 329 127 A | 3/1999 | | |
| GB | 2 333 965 A | 8/1999 | | |
| JP | 4129536 B2 | 8/2008 | | |
| SG | 71559 | 4/2002 | | |
| WO | 80/02182 A1 | 10/1980 | | |
| WO | 87/04626 A1 | 8/1987 | | |
| WO | 90/010424 A1 | 9/1990 | | |
| WO | 93/009727 A1 | 5/1993 | | |
| WO | 94/20041 A1 | 9/1994 | | |
| WO | 96/05873 A1 | 2/1996 | | |
| WO | 97/18007 A1 | 5/1997 | | |
| WO | 99/13793 A1 | 3/1999 | | |
| WO | WO-2017004423 A1 * | 1/2017 | | A61M 1/73 |
| WO | 2018150268 A1 | 8/2018 | | |

OTHER PUBLICATIONS

"IPhone (1st generation)", Wikipedia, Accessed Jan. 10, 2022. (Year: 2022).*

"IPhone (1st generation)", Wikipedia, Accessed Jan. 10, 2022. (Year: 2022) (Year: 2022).*

Nisus Negative Pressure Wound Therapy System "Instructions for Use", Cork Medical Products, pp. 21-25, (Year: 2010) (Year: 2010).*

CD-ROM, Wikipedia, "https://en.wikipedia.org/wiki/CD-ROM", 2024 (Year: 2024).*

Code Definition and Meaning, Merriam-Webster, "https://www.merriam-webster.com/dictionary/code", 2024 (Year: 2024).*

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sept. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by

(56) References Cited

OTHER PUBLICATIONS

V. Ye Volkov et al. (Chuvashia State University, Cheboksary, U.S.S.R. 1986); pp. 94-96 (certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians; Jul. 2007.
International Search Report and Written Opinion for Corresponding Application No. PCT/US2019/049649, mailed Jan. 3, 2020.

* cited by examiner

600

610

VeraFlo
INSTILL: 50 cc
SOAK: 30s
VAC: 125 mmHg, DPC, 3:3 min, 10 min

SYSTEMS AND METHODS FOR SCHEDULING AND CONTROLLING WOUND THERAPY

RELATED APPLICATIONS

The present application claims the benefit, under 35 USC § 119(e), of the filing of U.S. Provisional Patent Application Ser. No. 62/727,403, entitled "Systems and Methods for Scheduling and Controlling Wound Therapy," filed Sep. 5, 2018, which is incorporated herein by reference for all purposes.

TECHNICAL FIELD

The invention set forth in the appended claims relates generally to tissue treatment systems and more particularly, but without limitation, to systems and methods for providing negative-pressure therapy with fluid instillation therapy and, more specifically, scheduling and controlling both the negative pressure therapy and the fluid instillation therapy.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

There is also widespread acceptance that cleansing a tissue site can be highly beneficial for new tissue growth. For example, a wound or a cavity can be washed out with a liquid solution for therapeutic purposes. These practices are commonly referred to as "irrigation" and "lavage" respectively. "Instillation" is another practice that generally refers to a process of slowly introducing fluid to a tissue site and leaving the fluid for a prescribed period of time before removing the fluid. For example, instillation of topical treatment solutions over a wound bed can be combined with negative-pressure therapy to further promote wound healing by loosening soluble contaminants in a wound bed and removing infectious material. As a result, soluble bacterial burden can be decreased, contaminants removed, and the wound cleansed.

While the clinical benefits of negative-pressure therapy and/or instillation therapy are widely known, improvements to therapy systems, components, and processes may benefit healthcare providers and patients.

BRIEF SUMMARY

New and useful systems, apparatuses, and methods for scheduling and controlling both negative pressure therapy and fluid instillation therapy in a negative-pressure therapy environment are set forth in the appended claims. Illustrative embodiments are also provided to enable a person skilled in the art to make and use the claimed subject matter.

More specifically, a method for using a therapy device for providing negative-pressure therapy and instillation therapy to a dressing is described. The method may comprise coupling a source of negative pressure and a source of instillation fluid to the dressing. The method may further comprise applying negative pressure to the dressing based on an initial therapy configuration, monitoring negative pressure parameters associated with the application of negative pressure to the dressing to identify negative pressure alarm conditions, and modifying the initial therapy configuration to generate a modified therapy configuration in response to negative pressure alarm conditions identified. The method may further comprise applying instillation fluid to the dressing based on the initial therapy configuration, monitoring instillation parameters associated with the application of instillation fluid to the dressing to identify instillation alarm conditions, and modifying the initial therapy configuration to generate a modified therapy configuration in response to instillation alarm conditions identified.

In some embodiments, the initial therapy configuration may comprise therapy settings selected from a group of negative pressure therapy settings including identification of a therapy device, a target pressure, a therapeutic range, a pressure control mode, and a cycle time. In some other embodiments, the initial therapy configuration may comprise therapy settings selected from a group of instillation therapy settings including identification of an instillation fluid, a fill volume, a dwell time, a fluid pressure, and a negative pressure/instillation ratio. In yet other embodiments, the initial therapy configuration may comprise therapy settings selected from a group of scheduling therapy settings including a daily regimen, a weekday regimen, and a weekend regimen for applying negative pressure and instillation fluid.

In some embodiments, the method may further comprise providing corrective action in response to identification of a negative pressure alarm condition prior to modifying the initial therapy configuration. In some other embodiments, the method may also comprise providing corrective action in response to identification of an instillation alarm condition prior to modifying the initial therapy configuration. In some embodiments, the method may further comprise encoding the initial therapy configuration to be stored on a code that is machine-readable, wherein the code is adaptable to be modified. Such method may further comprise printing the code on a label associated with the therapy device or a package associated with disposals used with the therapy device. In some embodiments, such method may further comprise transferring the code to the therapy device from a wireless mobile device.

Additionally, a therapy system for providing negative-pressure therapy and instillation therapy to a dressing is described. The therapy system may comprise a source of instillation fluid adapted to be coupled to the dressing for providing instillation fluid to the dressing, and a source of negative pressure adapted to be coupled to the dressing for providing negative pressure to the dressing based on an initial therapy configuration. The therapy system may further comprise negative pressure sensors configured to monitor negative pressure parameters associated with the application of negative pressure to the dressing to identify negative pressure alarm conditions. The therapy system may further comprise instillation sensors configured to monitor instillation parameters associated with the application of instillation fluid to the dressing to identify instillation alarm conditions. In some embodiments, the therapy system may further comprise a controller coupled to the source of instillation fluid, the source of negative pressure, the negative pressure sensors, and the instillation sensors. The controller may be adapted to identify negative pressure alarm conditions based on the negative pressure parameters and identify instillation alarm conditions based on the instillation parameters. The controller being further adapted to modify the initial therapy configuration in response to the negative pressure alarm conditions and the instillation alarm conditions.

In some embodiments, the controller is adapted further to provide corrective action in response to identification of a negative pressure alarm condition prior to modifying the initial therapy configuration. In some other embodiments, the controller is adapted further to provide corrective action in response to identification of an instillation pressure alarm condition prior to modifying the initial therapy configuration. In some embodiments, the initial therapy configuration may be stored as a code that is machine-readable, and wherein the code may be adaptable to be modified. In other embodiments, the therapy system may further comprise a wireless communication module for receiving and transmitting the code with a remote wireless device. In other embodiments, the therapy system may further comprise a display coupled to the controller and adapted to provide a readable version of the code.

Objectives, advantages, and a preferred mode of making and using the claimed subject matter may be understood best by reference to the accompanying drawings in conjunction with the following detailed description of illustrative embodiments.

DESCRIPTION OF EXAMPLE EMBODIMENTS

The following description of example embodiments provides information that enables a person skilled in the art to make and use the subject matter set forth in the appended claims, but it may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
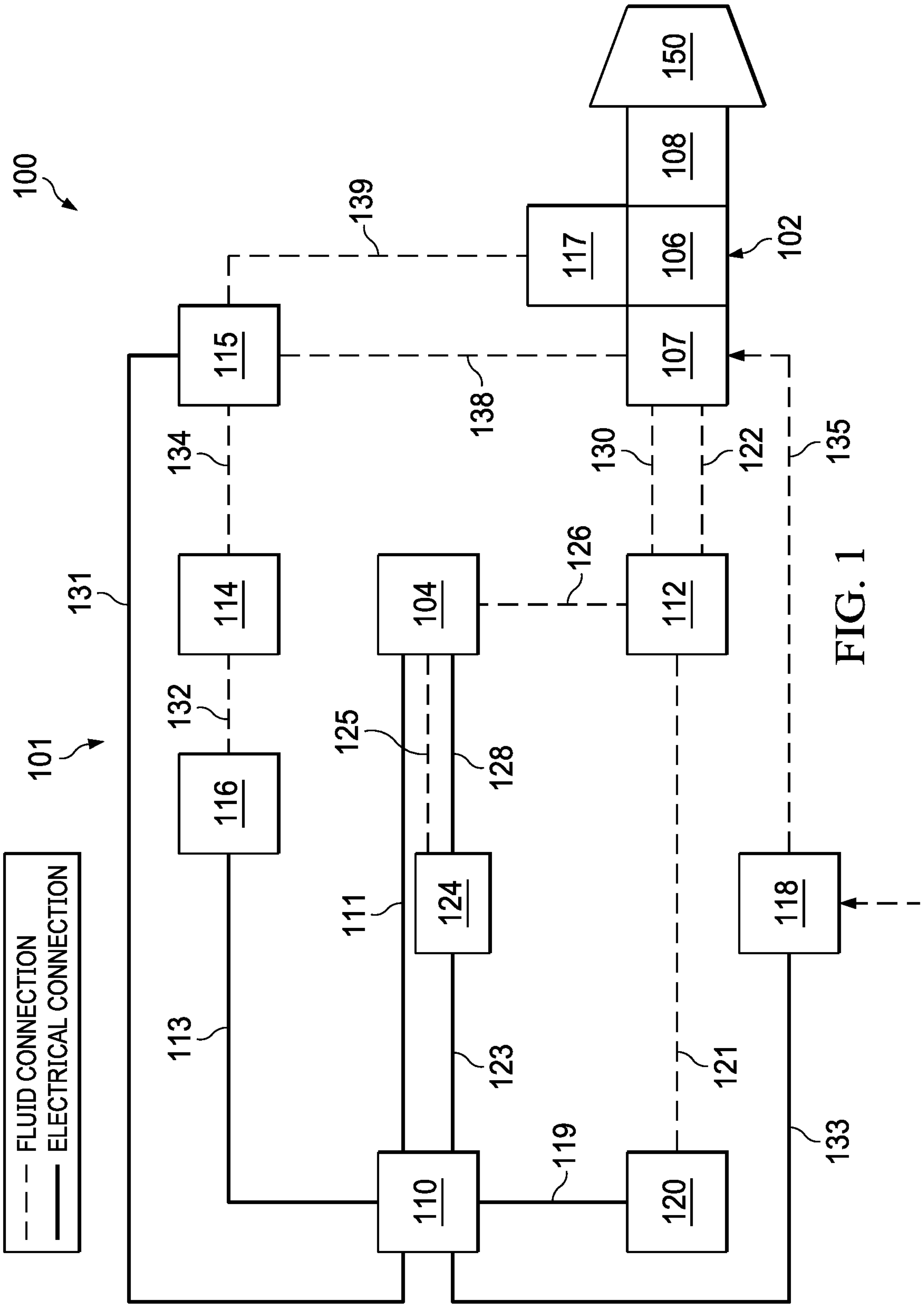
FIG. 1 is a functional block diagram of an example embodiment of a therapy system that can provide negative-pressure treatment and instillation treatment in accordance with this specification.

FIG. 1 is a simplified functional block diagram of an example embodiment of a therapy system 100 that can provide negative-pressure therapy with instillation of topical treatment solutions to a tissue site in accordance with this specification.

The term “tissue site” in this context broadly refers to a wound, defect, or other treatment target located on or within tissue, including, but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term “tissue site” may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted.

The therapy system 100 may include a negative-pressure supply, and may include or be configured to be coupled to a distribution component, such as a dressing. In general, a distribution component may refer to any complementary or ancillary component configured to be fluidly coupled to a negative-pressure supply between a negative-pressure supply and a tissue site. A distribution component is preferably detachable, and may be disposable, reusable, or recyclable. For example, a dressing 102 is illustrative of a distribution component that may be coupled to a negative-pressure source and other components.

The dressing 102 may be fluidly coupled to a negative-pressure source 104. A dressing may include a cover, a tissue interface, or both in some embodiments. The dressing 102, for example, may include a cover 106, a dressing interface 107, and a tissue interface 108. A computer or a controller device, such as a controller 110, may also be coupled to the negative-pressure source 104. In some embodiments, the cover 106 may be configured to cover the tissue interface 108 and the tissue site, and may be adapted to seal the tissue interface and create a therapeutic environment proximate to a tissue site for maintaining a negative pressure at the tissue site. In some embodiments, the dressing interface 107 may be configured to fluidly couple the negative-pressure source 104 to the therapeutic environment of the dressing. The therapy system 100 may optionally include a fluid container, such as a container 112, fluidly coupled to the dressing 102 and to the negative-pressure source 104.

The therapy system 100 may also include a source of instillation solution, such as a solution source 114. A distribution component may be fluidly coupled to a fluid path between a solution source and a tissue site in some embodiments. For example, an instillation pump 116 may be coupled to the solution source 114, as illustrated in the example embodiment of FIG. 1. The instillation pump 116 may also be fluidly coupled to the negative-pressure source 104. For example, in some embodiments, the instillation pump 116 may be fluidly coupled to the negative-pressure source 104 through the dressing 102. In some embodiments, the instillation pump 116 and the negative-pressure source 104 may be fluidly coupled to two different locations on the tissue interface 108 by two different dressing interfaces. For example, the negative-pressure source 104 may be fluidly coupled to the dressing interface 107 while the instillation pump 116 may be fluidly to the coupled to dressing interface 107 or a second dressing interface 117. In some other embodiments, the instillation pump 116 and the negative-pressure source 104 may be fluidly coupled to two different tissue interfaces by two different dressing interfaces, one dressing interface for each tissue interface (not shown).

The therapy system 100 may also include a regulator, such as an instillation regulator 115, that may also be fluidly coupled to the solution source 114 and the dressing 102 to ensure proper dosage of instillation solution (e.g. saline) to a tissue site. For example, the instillation regulator 115 may comprise a piston that can be pneumatically actuated by the negative-pressure source 104 to draw instillation solution from the solution source 114 during a negative-pressure interval and to instill the solution to a dressing during a venting interval. Additionally or alternatively, the controller 110 may be coupled to the negative-pressure source 104 by a conductor 111, the positive-pressure source 116 by a conductor 113, or both, to control dosage of instillation solution to a tissue site. In yet other embodiments, the regulator 115 may be coupled directly to the controller 110 as indicated by conductor 131. In still other embodiments, the instillation regulator 115 may also be fluidly coupled to the negative-pressure source 105 through the dressing 102.

The therapy system 100 also may include sensors to measure operating parameters and provide feedback signals to the controller 110 indicative of the operating parameters properties of fluids extracted from a tissue site. As illustrated in FIG. 1, for example, the therapy system 100 may include a pressure sensor or a control sensor 120, a pressure sensor or supply sensor 124, or both, coupled to the controller 110 by conductor 119 and conductor 123, respectively. The control sensor 120 may be fluidly coupled or configured to be fluidly coupled to a distribution component such as, for example, the dressing 102 either directly or indirectly through the container 112. The control sensor 120 may be configured to measure pressure being generated by the negative-pressure source 104 within the dressing 102, i.e., the therapy pressure for comparison to a desired therapy pressure such as, for example, a target pressure (TP) set by a user or clinician. The supply sensor 124 also may be coupled to the negative-pressure source 104 to measure the supply pressure (SP). In some example embodiments, the supply sensor 124 may be fluidly coupled proximate the output of the output of the negative-pressure source 104 as indicated by conductor 125 to directly measure the supply pressure (SP). In other example embodiments, the supply sensor 124 may be electrically coupled to the negative-pressure source 104 as indicated by conductor 126 to measure the changes in the current in order to determine the supply pressure (SP).

Distribution components may be fluidly coupled to each other to provide a distribution system for transferring fluids (i.e., liquid and/or gas). For example, a distribution system may include various combinations of fluid conductors and fittings to facilitate fluid coupling. A fluid conductor generally includes any structure with one or more lumina adapted to convey a fluid between two ends, such as a tube, pipe, hose, or conduit. Typically, a fluid conductor is an elongated, cylindrical structure with some flexibility, but the geometry and rigidity may vary. Some fluid conductors may be molded into or otherwise integrally combined with other components. A fitting can be used to mechanically and fluidly couple components to each other. For example, a fitting may comprise a projection and an aperture. The projection may be configured to be inserted into a fluid conductor so that the aperture aligns with a lumen of the fluid conductor. A valve is a type of fitting that can be used to control fluid flow. For example, a check valve can be used to substantially prevent return flow. A port is another example of a fitting. A port may also have a projection, which may be threaded, flared, tapered, barbed, or otherwise configured to provide a fluid seal when coupled to a component.

In some embodiments, distribution components may also be coupled by virtue of physical proximity, being integral to a single structure, or being formed from the same piece of material. Coupling may also include mechanical, thermal, electrical, or chemical coupling (such as a chemical bond) in some contexts. For example, a tube may mechanically and fluidly couple the dressing 102 to the container 112 in some embodiments. In general, components of the therapy system 100 may be coupled directly or indirectly. For example, the negative-pressure source 104 may be directly coupled to the controller 110, and may be indirectly coupled to the dressing interface 107 through the container 112 by conduit 126 and conduit 130. The control sensor 120 may be fluidly coupled to the dressing 102 directly (not shown) or indirectly by conduit 121 and conduit 122. Additionally, the instillation pump 116 may be coupled indirectly to the dressing interface 107 through the solution source 114 and the instillation regulator 115 by fluid conductors 132, 134 and 138. Alternatively, the instillation pump 116 may be coupled indirectly to the second dressing interface 117 through the solution source 114 and the instillation regulator 115 by fluid conductors 132, 134 and 139.

"Negative pressure" generally refers to a pressure less than a local ambient pressure, such as the ambient pressure in a local environment external to a sealed therapeutic environment provided by the dressing 102. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. Similarly, references to increases in negative pressure typically refer to a decrease in absolute pressure, while decreases in negative pressure typically refer to an increase in absolute pressure. While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −75 mm Hg (−9.9 kPa) and −300 mm Hg (−39.9 kPa).

A negative-pressure supply, such as the negative-pressure source 104, may be a reservoir of air at a negative pressure, or may be a manual or electrically-powered device that can reduce the pressure in a sealed volume, such as a vacuum pump, a suction pump, a wall suction port available at many healthcare facilities, or a micro-pump, for example. A negative-pressure supply may be housed within or used in conjunction with other components, such as sensors, processing units, alarm indicators, memory, databases, software, display devices, or user interfaces that further facilitate therapy. For example, in some embodiments, the negative-pressure source 104 may be combined with the controller 110 and other components into a therapy unit. A negative-pressure supply may also have one or more supply ports configured to facilitate coupling and de-coupling the negative-pressure supply to one or more distribution components.

The tissue interface 108 can be generally adapted to contact a tissue site such as, for example, a tissue site 150. The tissue interface 108 may be partially or fully in contact with the tissue site. If the tissue site is a wound, for example, the tissue interface 108 may partially or completely fill the wound, or may be placed over the wound. The tissue interface 108 may take many forms, and may have many sizes, shapes, or thicknesses depending on a variety of factors, such as the type of treatment being implemented or the nature and size of a tissue site. For example, the size and shape of the tissue interface 108 may be adapted to the contours of deep and irregular shaped tissue sites. Moreover, any or all of the surfaces of the tissue interface 108 may have projections or an uneven, course, or jagged profile that can induce strains and stresses on a tissue site, which can promote granulation at the tissue site.

In some embodiments, the tissue interface 108 may be a manifold. A "manifold" in this context generally includes any substance or structure providing a plurality of pathways adapted to collect or distribute fluid across a tissue site under pressure. For example, a manifold may be adapted to receive negative pressure from a source and distribute negative pressure through multiple apertures across a tissue site, which may have the effect of collecting fluid from across a tissue site and drawing the fluid toward the source. In some embodiments, the fluid path may be reversed or a secondary fluid path may be provided to facilitate delivering fluid across a tissue site.

In some illustrative embodiments, the pathways of a manifold may be interconnected to improve distribution or collection of fluids across a tissue site. In some illustrative embodiments, a manifold may be a porous foam material having interconnected cells or pores. For example, cellular foam, open-cell foam, reticulated foam, porous tissue collections, and other porous material such as gauze or felted mat generally include pores, edges, and/or walls adapted to form interconnected fluid channels. Liquids, gels, and other foams may also include or be cured to include apertures and fluid pathways. In some embodiments, a manifold may additionally or alternatively comprise projections that form interconnected fluid pathways. For example, a manifold may be molded to provide surface projections that define interconnected fluid pathways.

In some embodiments, the tissue interface 108 may comprise or consist essentially of reticulated foam having pore sizes and free volume that may vary according to needs of a prescribed therapy. For example, reticulated foam having a free volume of at least 90% may be suitable for many therapy applications, and foam having an average pore size in a range of 400-600 microns (40-50 pores per inch) may be particularly suitable for some types of therapy. The tensile strength of the tissue interface 108 may also vary according to needs of a prescribed therapy. For example, the tensile strength of foam may be increased for instillation of topical treatment solutions. The 25% compression load deflection of the tissue interface 108 may be at least 0.35 pounds per square inch, and the 65% compression load deflection may be at least 0.43 pounds per square inch. In some embodiments, the tensile strength of the tissue interface 108 may be at least 10 pounds per square inch. The tissue interface 108 may have a tear strength of at least 2.5 pounds per inch. In some embodiments, the tissue interface may be foam comprised of polyols such as polyester or polyether, isocyanate such as toluene diisocyanate, and polymerization modifiers such as amines and tin compounds. In some examples, the tissue interface 108 may be reticulated polyurethane foam such as found in GRANUFOAM™ dressing or V.A.C. VERAFLO™ dressing, both available from Kinetic Concepts, Inc. of San Antonio, Texas.

The thickness of the tissue interface 108 may also vary according to needs of a prescribed therapy. For example, the thickness of the tissue interface may be decreased to reduce tension on peripheral tissue. The thickness of the tissue interface 108 can also affect the conformability of the tissue interface 108. In some embodiments, a thickness in a range of about 5 millimeters to 10 millimeters may be suitable.

The tissue interface 108 may be either hydrophobic or hydrophilic. In an example in which the tissue interface 108 may be hydrophilic, the tissue interface 108 may also wick fluid away from a tissue site, while continuing to distribute negative pressure to the tissue site. The wicking properties of the tissue interface 108 may draw fluid away from a tissue site by capillary flow or other wicking mechanisms. An example of a hydrophilic foam is a polyvinyl alcohol, open-cell foam such as V.A.C. WhiteFoam® dressing available from Kinetic Concepts, Inc. of San Antonio, Texas. Other hydrophilic foams may include those made from polyether. Other foams that may exhibit hydrophilic characteristics include hydrophobic foams that have been treated or coated to provide hydrophilicity.

The tissue interface 108 may further promote granulation at a tissue site when pressure within the sealed therapeutic environment is reduced. For example, any or all of the surfaces of the tissue interface 108 may have an uneven, coarse, or jagged profile that can induce microstrains and stresses at a tissue site if negative pressure is applied through the tissue interface 108.

In some embodiments, the tissue interface 108 may be constructed from bioresorbable materials. Suitable bioresorbable materials may include, without limitation, a polymeric blend of polylactic acid (PLA) and polyglycolic acid (PGA). The polymeric blend may also include without limitation polycarbonates, polyfumarates, and capralactones. The tissue interface 108 may further serve as a scaffold for new cell-growth, or a scaffold material may be used in conjunction with the tissue interface 108 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In some embodiments, the cover 106 may provide a bacterial barrier and protection from physical trauma. The cover 106 may also be constructed from a material that can reduce evaporative losses and provide a fluid seal between two components or two environments, such as between a therapeutic environment and a local external environment. The cover 106 may be, for example, an elastomeric film or membrane that can provide a seal adequate to maintain a negative pressure at a tissue site for a given negative-pressure source. The cover 106 may have a high moisture-vapor transmission rate (MVTR) in some applications. For example, the MVTR may be at least 300 g/m^2 per twenty-four hours in some embodiments. In some example embodiments, the cover 106 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained.

An attachment device may be used to attach the cover 106 to an attachment surface, such as undamaged epidermis, a gasket, or another cover. The attachment device may take many forms. For example, an attachment device may be a medically-acceptable, pressure-sensitive adhesive that extends about a periphery, a portion, or an entire sealing member. In some embodiments, for example, some or all of the cover 106 may be coated with an acrylic adhesive having a coating weight between 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

In some embodiments, the dressing interface 107 may facilitate coupling the negative-pressure source 104 to the dressing 102. The negative pressure provided by the negative-pressure source 104 may be delivered through the conduit 130 to a negative-pressure interface, which may include an elbow portion. In one illustrative embodiment, the negative-pressure interface may be a T.R.A.C.® Pad or Sensa T.R.A.C.® Pad available from KCl of San Antonio, Texas. The negative-pressure interface enables the negative pressure to be delivered through the cover 106 and to the tissue interface 108 and the tissue site. In this illustrative, non-limiting embodiment, the elbow portion may extend through the cover 106 to the tissue interface 108, but numerous arrangements are possible.

A controller, such as the controller 110, may be a microprocessor or computer programmed to operate one or more components of the therapy system 100, such as the negative-pressure source 104. In some embodiments, for example, the controller 110 may be a microcontroller, which generally comprises an integrated circuit containing a processor core and a memory programmed to directly or indirectly control one or more operating parameters of the therapy system 100. Operating parameters may include the power applied to the negative-pressure source 104, the pressure generated by the negative-pressure source 104, or the pressure distributed to the tissue interface 108, for example. The controller 110 is also preferably configured to receive one or more input signals, such as a feedback signal, and programmed to modify one or more operating parameters based on the input signals.

Sensors, such as the control sensor 120 or the supply sensor 124, are generally known in the art as any apparatus operable to detect or measure a physical phenomenon or property, and generally provide a signal indicative of the phenomenon or property that is detected or measured. For example, the control sensor 120 and the supply sensor 124 may be configured to measure one or more operating parameters of the therapy system 100. In some embodiments, the control sensor 120 may be a transducer configured to measure pressure in a pneumatic pathway and convert the measurement to a signal indicative of the pressure measured. In some embodiments, for example, the control sensor 120 may be a piezoresistive strain gauge. The supply sensor 124 may optionally measure operating parameters of the negative-pressure source 104, such as the voltage or current, in some embodiments. Preferably, the signals from the control sensor 120 and the supply sensor 124 are suitable as an input signal to the controller 110, but some signal conditioning may be appropriate in some embodiments. For example, the signal may need to be filtered or amplified before it can be processed by the controller 110.

The solution source 114 is representative of a container, canister, pouch, bag, or other storage component, which can provide a solution for instillation therapy. Compositions of solutions may vary according to a prescribed therapy, but examples of solutions that may be suitable for some prescriptions include hypochlorite-based solutions, silver nitrate (0.5%), sulfur-based solutions, biguanides, cationic solutions, and isotonic solutions. Examples of such other therapeutic solutions that may be suitable for some prescriptions include hypochlorite-based solutions, silver nitrate (0.5%), sulfur-based solutions, biguanides, cationic solutions, and isotonic solutions. In one illustrative embodiment, the solution source 114 may include a storage component for the solution and a separate cassette for holding the storage component and delivering the solution to the tissue site 150, such as a V.A.C. VeraLink™ Cassette available from Kinetic Concepts, Inc. of San Antonio, Texas.

The container 112 may also be representative of a container, canister, pouch, or other storage component, which can be used to collect and manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy. In some embodiments, the container 112 may comprise a canister having a collection chamber, a first inlet fluidly coupled to the collection chamber and a first outlet fluidly coupled to the collection chamber and adapted to receive negative pressure from a source of negative pressure. In some embodiments, a first fluid conductor may comprise a first member such as, for example, the conduit 130 fluidly coupled between the first inlet and the tissue interface 108 by the negative-pressure interface described above, and a second member such as, for example, the conduit 126 fluidly coupled between the first outlet and a source of negative pressure whereby the first conductor is adapted to provide negative pressure within the collection chamber to the tissue site.

The therapy system 100 may also comprise a flow regulator such as, for example, a regulator 118 fluidly coupled to a source of ambient air to provide a controlled or managed flow of ambient air to the sealed therapeutic environment provided by the dressing 102 and ultimately the tissue site. In some embodiments, the regulator 118 may control the flow of ambient fluid to purge fluids and exudates from the sealed therapeutic environment. In some embodiments, the regulator 118 may be fluidly coupled by a fluid conductor or vent conduit 135 through the dressing interface 107 to the tissue interface 108. The regulator 118 may be configured to fluidly couple the tissue interface 108 to a source of ambient air as indicated by a dashed arrow. In some embodiments, the regulator 118 may be disposed within the therapy system 100 rather than being proximate to the dressing 102 so that the air flowing through the regulator 118 is less susceptible to accidental blockage during use. In such embodiments, the regulator 118 may be positioned proximate the container 112 and/or proximate a source of ambient air where the regulator 118 is less likely to be blocked during usage. In some embodiments, the controller 110 may be electrically coupled to the regulator 118 by conductor 133 to control the flow of ambient fluid to purge fluids and exudates from the sealed therapeutic environment. For example, the controller 110 may activate the regulator 118 to evacuate the sealed therapeutic environment from fluids and exudates more quickly to initiate negative pressure therapy after instillation therapy.

The therapy system 100 may be packaged as a single, integrated unit such as a therapy system including many of the components shown in FIG. 1 that may be referred to collectively as a therapy device that is fluidly coupled to the dressing 102. For example, one example embodiment of the therapy system 100 may provide both negative pressure therapy and instillation therapy and comprise a therapy device 101 including all the distribution components described above that are fluidly coupled to the dressing 102. In some example embodiments of the therapy system 100, the container 112 may be a detachable distribution component separate from the therapy device 101. The therapy device 101 may be, for example, a V.A.C. Ulta™ System available from Kinetic Concepts, Inc. of San Antonio, Texas.

In operation, the tissue interface 108 may be placed within, over, on, or otherwise proximate a tissue site, such as tissue site 150. The cover 106 may be placed over the tissue interface 108 and sealed to an attachment surface near the tissue site 150. For example, the cover 106 may be sealed to undamaged epidermis peripheral to a tissue site. Thus, the dressing 102 can provide a sealed therapeutic environment proximate to a tissue site, substantially isolated from the external environment, and the negative-pressure source 104 can reduce the pressure in the sealed therapeutic environment. Negative pressure applied across the tissue site through the tissue interface 108 in the sealed therapeutic environment can induce macrostrain and microstrain in the tissue site, as well as remove exudates and other fluids from the tissue site, which can be collected in container 112.

The fluid mechanics of using a negative-pressure source to reduce pressure in another component or location, such as within a sealed therapeutic environment, can be mathematically complex. However, the basic principles of fluid mechanics applicable to negative-pressure therapy and instillation are generally well-known to those skilled in the art, and the process of reducing pressure may be described illustratively herein as "delivering," "distributing," or "generating" negative pressure, for example.

In general, exudate and other fluid flow toward lower pressure along a fluid path. Thus, the term "downstream" typically implies something in a fluid path relatively closer to a source of negative pressure or further away from a source of positive pressure. Conversely, the term "upstream" implies something relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications, such as by substituting a positive-pressure source for a negative-pressure source, and this descriptive convention should not be construed as a limiting convention.

In one embodiment, the controller 110 may receive and process data, such as data related to the pressure distributed to the tissue interface 108 from the control sensor 120. The controller 110 may also control the operation of one or more components of therapy system 100 to manage the pressure distributed to the tissue interface 108 for application to the wound and/or incision at the tissue site 150, which may also be referred to as a control pressure (CP). In one embodiment, controller 110 may include an input for receiving a desired target pressure (TP) set by a clinician or other user and may be program for processing data relating to the setting and inputting of the target pressure (TP) to be applied to the tissue site 150. In one example embodiment, the target pressure (TP) may be a fixed pressure value determined by a user/caregiver as the reduced pressure target desired for therapy at the tissue site 150 and then provided as input to the controller 110. The user may be a nurse or a doctor or other approved clinician who prescribes the desired negative pressure to which the tissue site 150 should be applied. The desired negative pressure may vary from tissue site to tissue site based on the type of tissue forming the tissue site 150, the type of injury or wound (if any), the medical condition of the patient, and the preference of the attending physician. After selecting the desired target pressure (TP), the negative-pressure source 104 is controlled to achieve the target pressure (TP) desired for application to the tissue site 150.

Figure 2:
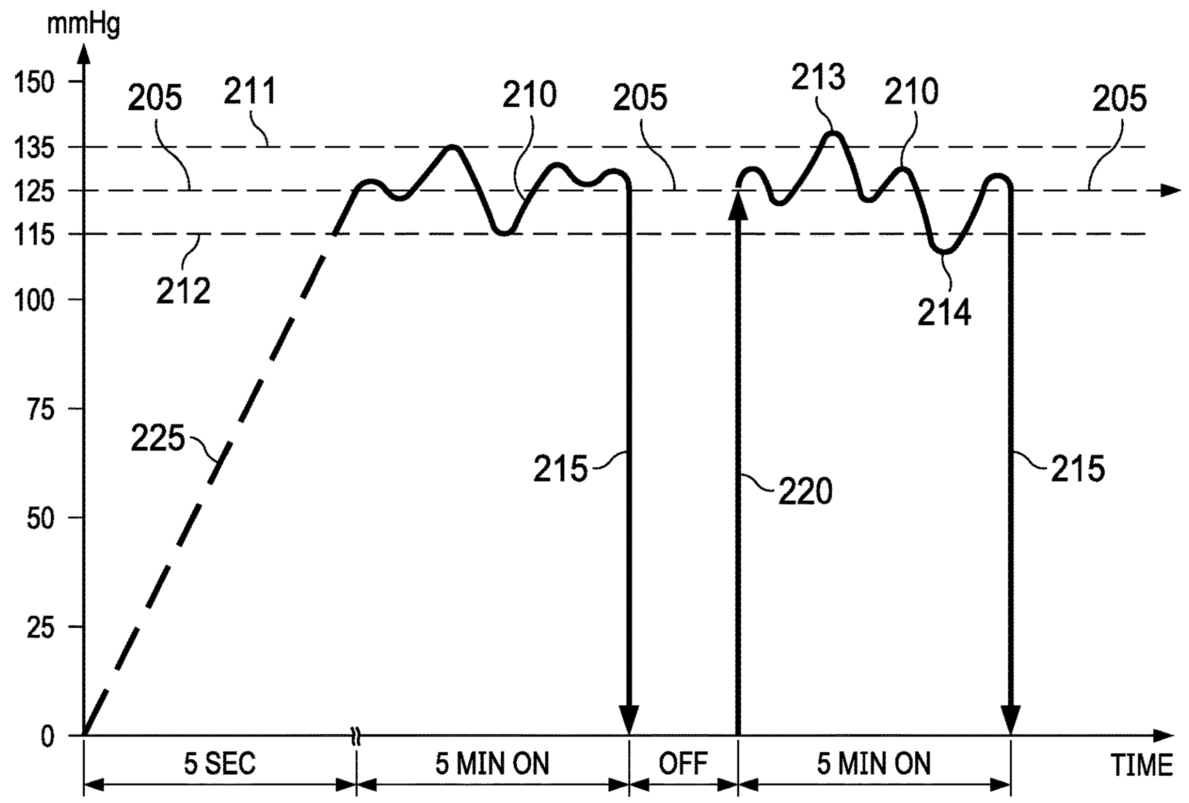
FIG. 2 is a graph illustrating additional details of example pressure control modes that may be associated with some embodiments of the therapy system of FIG. 1.

FIG. 2 is a graph illustrating additional details of an example control mode that may be associated with some embodiments of the controller 110 for providing negative pressure to a dressing. In some embodiments, the controller 110 may have a continuous pressure mode, in which the negative-pressure source 104 is operated to provide a constant target negative pressure, i.e., the target pressure (TP) as indicated by dashed line 205, for the duration of treatment or until manually deactivated. Additionally or alternatively, the controller 110 may have an intermittent pressure mode, as also illustrated in the example of FIG. 2. In FIG. 2, the x-axis represents time and the y-axis represents negative pressure generated by the negative-pressure source 104 over time. In the example of FIG. 2, the controller 110 can operate the negative-pressure source 104 to cycle between the target pressure (TP) and atmospheric pressure. For example, the target pressure may be set at a value of 125 mmHg, as indicated by the dashed line 205, for a specified period of time (e.g., 5 min), followed by a specified period of time (e.g., 2 min) of deactivation, as indicated by the gap between solid lines 215 and 220. The cycle can be repeated by activating the negative-pressure source 104, as indicated by line 220, which can form a square wave pattern between the target pressure (TP) and atmospheric pressure. In some embodiments, the ratio of the "on-time" to the "off-time" or the total "cycle time" may be referred to as a pump duty cycle (PD). In some embodiments, the negative-pressure source 104 may be operated manually or automatically to deactivate the application of negative pressure to the dressing 102. In some embodiments, deactivation may be accelerated by utilizing the regulator 118 to vent the dressing 102 to the atmosphere.

In some example embodiments, the increase in negative-pressure from ambient pressure to the target pressure may not be instantaneous. For example, the negative-pressure source 104 and the dressing 102 may have an initial rise time, as indicated by the dashed line 225. The initial rise time may vary depending on the type of dressing and therapy equipment being used. For example, the initial rise time for one therapy system may be in a range of about 20-30 mmHg/second and in a range of about 5-10 mmHg/second for another therapy system. If the therapy system 100 is operating in an intermittent mode, the repeating rise time, as indicated by the solid line 220, may be a value substantially equal to the initial rise time as indicated by the dashed line 225. When the controller 110 is operating in the intermittent mode, the rise time after the initial rise time as indicated by the solid line 220 may be a value substantially equal to the initial rise time as indicated by the dashed line 225.

In some example embodiments, the negative-pressure provided by the negative-pressure source 104, i.e., the supply pressure (SP), may vary around the target pressure (TP) and a therapeutic range (TR) relative to the target pressure (TP) may be desired for limiting variations in the supply pressure (SP). For example, the supply pressure (SP) may vary around a target pressure (TP) of about −125 mmHg as indicated by solid line 210, and the therapeutic range (TR) that is desired may have a tolerance of about 10 mmHg above and/or below the target pressure (TP). Thus, the supply pressure (SP) is within the therapeutic range (TR) if the supply pressure (SP) is not greater than an upper limit and/or less than a lower limit. Continuing with the example, the upper limit of the therapeutic range would be −135 mmHg indicated by the dashed line 211. Additionally, the supply pressure during the first five minute "on-cycle" remains within the therapeutic range (TR) because the supply pressure is not greater than the upper limit of the therapeutic range, whereas a reduced pressure of −137 mm Hg indicated at 213 during the second five minute on-cycle is greater than the upper limit of the therapeutic range. Correspondingly, the lower limit of the therapeutic range would be −115 mmHg indicated by the dashed line 212. The supply pressure during the first five minute "on-cycle" remains within the therapeutic range (TR) because the supply pressure is not less than the lower limit of the therapeutic range, whereas a reduced pressure of −113 mm Hg indicated at 214 during the second five minute on-cycle is less than the lower limit of the therapeutic range.

Figure 3:
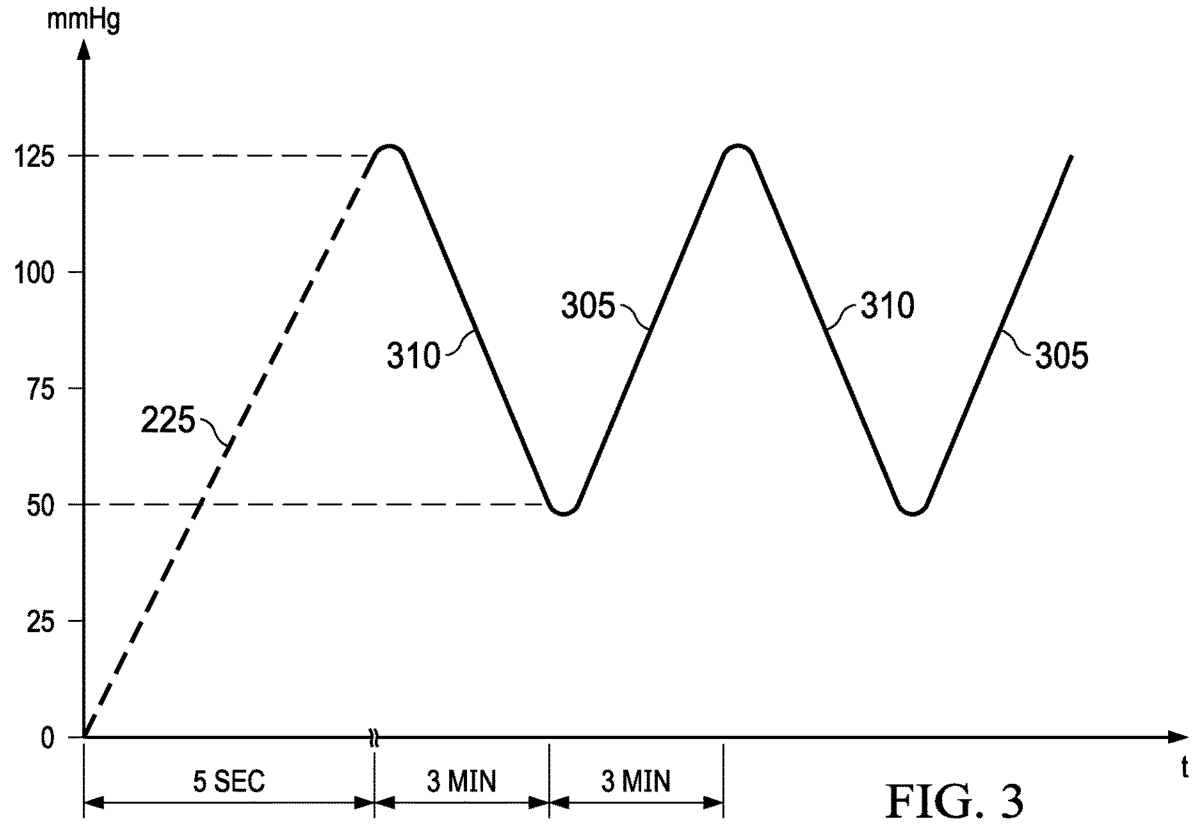
FIG. 3 is a graph illustrating additional details that may be associated with another example pressure control mode in some embodiments of the therapy system of FIG. 1.

FIG. 3 is a graph illustrating additional details that may be associated with another example pressure control mode in some embodiments of the therapy system 100. In FIG. 3, the x-axis represents time and the y-axis represents negative pressure generated by the negative-pressure source 104. The target pressure in the example of FIG. 3 can vary with time in a dynamic pressure mode. For example, the target pressure may vary in the form of a triangular waveform, varying between a negative pressure of 50 and 135 mmHg with a rise time 305 set at a rate of +25 mmHg/min. and a descent time 310 set at −25 mmHg/min. In other embodiments of the therapy system 100, the triangular waveform may vary between negative pressure of 25 and 135 mmHg with a rise time 305 set at a rate of +30 mmHg/min and a descent time 310 set at −30 mmHg/min.

In some embodiments, the controller 110 may control or determine a variable target pressure (VTP) in a dynamic pressure mode, and the variable target pressure may vary between a maximum and minimum pressure value that may be set as an input prescribed by an operator as the range of desired negative pressure. The variable target pressure may also be processed and controlled by the controller 110, which can vary the target pressure according to a predetermined waveform, such as a triangular waveform, a sine waveform, or a saw-tooth waveform. In some embodiments, the waveform may be set by an operator as the predetermined or time-varying negative pressure desired for therapy.

Figure 4:
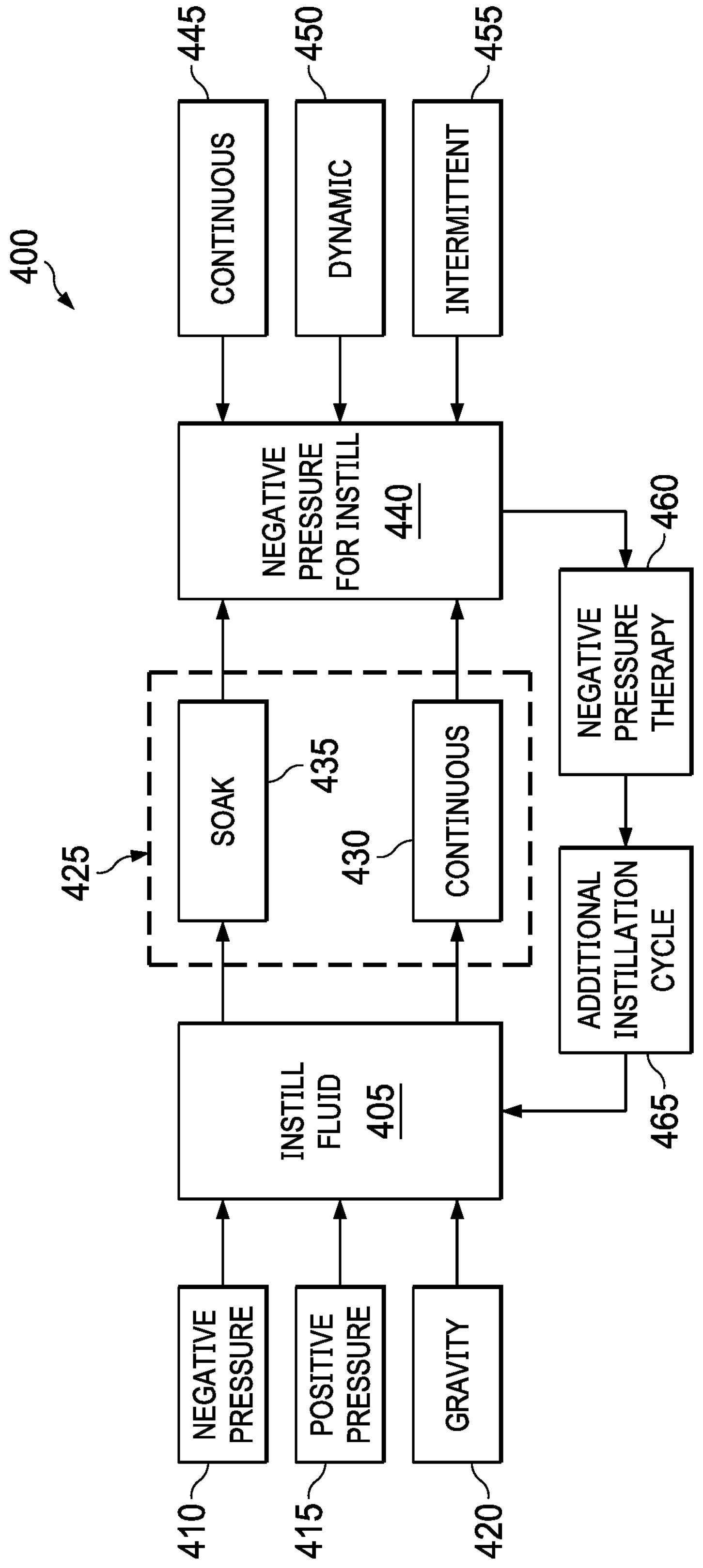
FIG. 4 is a chart illustrating details that may be associated with an example method of operating the therapy system of FIG. 1.

FIG. 4 is a chart illustrating details that may be associated with an example method 400 of operating the therapy system 100 to provide negative-pressure treatment and instillation treatment to the tissue interface 108. In some embodiments, the controller 110 may receive and process data, such as data related to instillation solution provided to the tissue interface 108. Such data may include the type of instillation solution prescribed by a clinician, the volume of fluid or solution to be instilled to a tissue site ("fill volume"), and the amount of time prescribed for leaving solution at a tissue site ("dwell time") before applying a negative pressure to the tissue site. The fill volume may be, for example, between 10 and 500 mL, and the dwell time may be between one second to 30 minutes. The controller 110 may also control the operation of one or more components of the therapy system 100 to instill solution, as indicated at 405. For example, the controller 110 may manage fluid distributed from the solution source 114 to the tissue interface 108. In some embodiments, fluid may be instilled to a tissue site by applying a negative pressure from the negative-pressure source 104 to reduce the pressure at the tissue site, drawing solution into the tissue interface 108, as indicated at 410. In some embodiments, solution may be instilled to a tissue site by applying a positive pressure from the positive-pressure source 116 to move solution from the solution source 114 to the tissue interface 108 is indicated at 415. Additionally or alternatively, the solution source 145 may be elevated to a height sufficient to allow gravity to move solution into the tissue interface 108 as indicated at 420.

The controller 110 may also control the fluid dynamics of instillation at 425 by providing a continuous flow of solution at 430 or an intermittent flow of solution at 435. Negative pressure may be applied to provide either continuous flow or intermittent flow of solution at 440. The application of negative pressure may be implemented to provide a continuous pressure mode of operation at 445 to achieve a continuous flow rate of instillation solution through the tissue interface 108, it may be implemented to provide a dynamic pressure mode of operation at 450 to vary the flow rate of instillation solution through the tissue interface 108. Alternatively, the application of negative pressure may be implemented to provide an intermittent mode of operation at 455 to allow instillation solution to dwell at the tissue interface 108. In an intermittent mode, a specific fill volume and dwell time may be provided depending, for example, on the type of tissue site being treated and the type of dressing being utilized. After or during instillation of solution, negative-pressure treatment may be applied at 460. The controller 110 may be utilized to select a mode of operation and the duration of the negative pressure treatment before commencing another instillation cycle at 465 by instilling more solution at 405.

Figures 5, 6A, 6B:
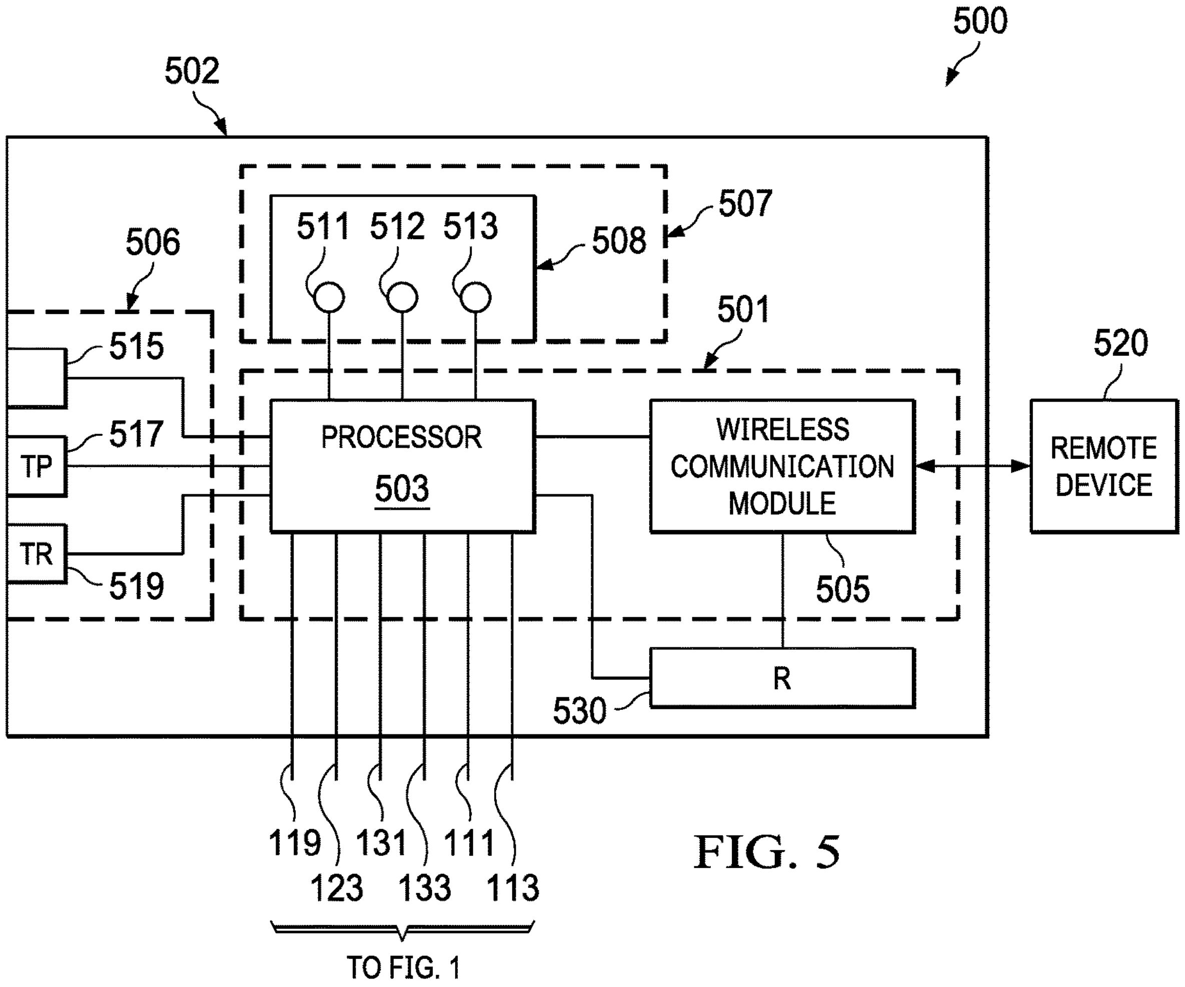
FIG. 5 is a schematic illustrating additional details of an example embodiment of a controller that may be associated with some embodiments of the therapy system of FIG. 1.
FIG. 6A is a QR code illustrating additional details of an example embodiment of a barcode that may be associated with some embodiments of the therapy system of FIG. 1.
FIG. 6B is information stored by the QR code.

FIG. 5 is a schematic view illustrating an example embodiment of a controller 500 that may be used with some embodiments of the therapy system 100 including the features of the controller 110 as described above. In some embodiments, the controller 500 may comprise a communication module 501 mounted on a printed circuit board 502. The communication module 501 may comprise a processor 503 and/or a wireless communication module 505 to enable wireless communication with other components of the therapy system 100 or other peripheral devices located remote from the therapy system 100. In some other embodiments, the processor 503 and the wireless communication module 505 may be separate components. In some embodiments, the controller 500 may further comprise therapy inputs 506 that may be coupled to input ports of the processor 503. The processor 503 also may comprise other input ports that may be coupled to other input devices such as, for example, the control sensor 120 and the supply sensor 124. In some embodiments, the controller 500 may further comprise therapy outputs 507 that may be coupled to output ports of the processor 503. The printed circuit board 502 may be an electronic device having one or more electronic components electrically coupled by conductive pathways. The printed circuit board 502 may include electrical conductors and electronic components such as capacitors, resistors, or other active devices mounted on or within the printed circuit board. In some embodiments, the printed circuit board 502 may be coupled directly or indirectly to the components as an upgrade for monitoring and/or controlling the operation of the regulators 115 and 118, the negative pressure source 104, or the instillation pump 116, or any other mechanical component used in conjunction with a therapy system similar to the therapy system 100.

In some embodiments, the printed circuit board 502 may include a power supply or electric potential source (not shown) for providing voltage to the components mounted on the printed circuit board 502. In some embodiments, the printed circuit board 502 also may include a signal interface or indicator electrically coupled to outputs of the processor 503 such as, for example, therapy outputs 507, that provides some indication of the signal to a user of the therapy system 100. In some embodiments, the indicator may be a visual device, such as a liquid crystal device (LCD) 508 or a light emitting diode (LED) 511, an auditory device, such as a speaker or auditory pulse emitter, a tactile device, such as a moving protrusion, or an olfactory device. In some embodiments, the indicator may be multiple devices such as, for example, a display comprising multiple LEDs emitting different wavelengths of light including, for example, LEDs 511, 512, and 513. The LCD 508 may be a display that presents images using the light-modulating properties of liquid crystals. In general, an LCD includes a layer of molecules aligned between two electrodes and two polarizing filters. Each filter has an axis of transmission that is perpendicular to the other so that when one filter is transparent, the other is not. A voltage may be applied to the electrodes, and in response the molecules of the layer are aligned to either block or allow the passage of light. An image is visible if light is blocked. The LCD 508 may be coupled to outputs of the processor 503 to receive a signal from the control sensor 120 and the supply sensor 124. In some embodiments, the LCD 508 may signal operating states and other information, such as a current pressure, a pressure differential, a leak condition, a blockage condition, an overpressure condition, or a canister full condition, for example.

The printed circuit board 502 may further include an electronic storage device, such as a memory, and other devices configured to operate the feedback system 500 such as, for example, other passive and active devices including input and output devices. In some embodiments, the printed circuit board 502 may include input devices such as, for example, switches or a touchscreen 515 for a user to provide settings for signals indicative of the therapy pressure (TP) and/or a therapeutic range (TR) as related to the therapy pressure (TP) to the processor 503. In some embodiments, the printed circuit board 502 may include a switch 517 and/or a switch 519 electrically coupled to input leads of the processor 503 for setting the processor with the desired therapy pressure (TP) and/or the desired therapeutic range (TR). In some embodiments, the printed circuit board 502 may include other input buffers or controllers needed by peripheral devices associated with the other components of therapy system 100 and/or the reduced pressure system 400.

In some embodiments, the controller 501 may be a single chip comprising the processor 503 and the wireless communication module 505 electrically coupled to the processor 503. Using a wireless communications module 505 provides an advantage of eliminating electrical conductors between the components of the therapy system 100 or remote peripheral devices when in use during therapy treatments. In some embodiments, for example, the electrical circuits and/or components associated with the control sensor 120, the supply sensor 124, the switch 517, the switch 519, and other inputs and output devices may be electrically coupled to other components of the therapy system 100 and other peripheral devices having wireless capability by wireless means such as, for example, an integrated device implementing Bluetooth® Low Energy wireless technology. More specifically, the wireless communication module 505 may be a Bluetooth® Low Energy system-on-chip that includes a microprocessor (an example of the microprocessors referred to hereinafter) such as the nRF51822 chip available from Nordic Semiconductor. The wireless communications module 505 may be implemented with other wireless technologies suitable for use in the medical environment such as radio frequency identification (RFID). In some embodiments, for example, the wireless communications module 505 may include wireless communication technologies that not only provide operators with a method of retrieving therapy data such as therapy duration, pressures, and alarm conditions, but also provide closed-loop feedback to the processor 503 for automatically adjusting and correcting pressure parameters that control the components of the therapy system 100 to provide negative pressure therapy and instillation therapy.

As described above, the processor 503 may display a numerical value on the LCD 508 corresponding to the pressure determined by the control sensor 120. In some embodiments, the numerical value may change as the pressure changes. It should be understood, that any signals provided by outputs of the processor 503 also may be transmitted by the wireless communication module 505 to other remote devices such as, for example, the remote device 520. Thus, any reference herein to signals being provided to the LCD 508 also applies to signals being provided to other devices not mounted on the printed circuit board 502. Moreover, any pressure measurements provided by either the control sensor 120 or the supply sensor 124 to the processor 503 may be stored therein for further processing relating to the target pressure (TP), the therapeutic range (TR), and the operating states of the therapy system 100 including a current pressure, a pressure differential, a leak condition, a blockage condition, a canister full condition, or an overpressure condition, for example.

In some example embodiments, therapy configuration information comprising a variety of therapy settings and operating parameters relating to a therapy device such as, for example, therapy device 101, may be encoded and stored in memory on the processor 503 or the remote device 520, for example, in a standard bar code format (GA1-128/EAN-128) or standard QR code (ISO 18004). A standard barcode or a QR code is a machine-readable optical label that contains information about the item to which it is attached. In some example embodiments, such therapy configuration information stored in a code may be retrieved using a standard barcode or QR reader such as, for example, the reader 530 and/or the remote device 520. In some example embodiments, a QR code storing information regarding the therapy configuration may be attached to various components of therapy system 100 such as, for example, the therapy device 101 and/or packages containing disposables utilized with the device 101 such as, for example, the dressing 102. Respecting the device 101, a QR code storing such information may be printed on a laminated card tethered to the therapy device 101 in some embodiments, or on a label stuck to the therapy device 101 in other embodiments. In yet other embodiments, the QR code storing such information may be displayed on the LCD 508 of the therapy device 101 that can be decoded by a QR reader. Regarding packages containing disposables, a QR code may be printed directly on the package specify the type of therapy device for intended use with the disposables such as, for example, the dressing 102 that is usable with the therapy device 101.

Therapy configurations may be complex to treat a tissue site because they comprise a variety of initial therapy settings depending on the desired therapy, and they may need to be modified during the course of treatment. Using a QR code to store and retrieve more complex therapy configurations regarding such therapy devices and packages provides a distinct advantage because of the enhanced speed and accuracy associated with providing therapy to patients in acute care situations. QR codes may be encoded or generated to store templates containing the initial therapy settings and adaptable to be subsequently modified if necessary depending on the progress of the treatments. In some embodiments, therapy templates comprising initial therapy settings may be customized for a specific supplier or user of the therapy device/or package of disposables. For example, a therapy template may be specifically encoded the manufacturer or supplier of the therapy device or package of disposables. In other embodiments, a therapy template may be customized for a specific healthcare system, a hospital, or a wing of a hospital for use in a particular environment. In some embodiments, these therapy templates may also be customized for specific locations such as, for example, hospitals in different cities or states. In some embodiments, therapy templates comprising initial therapy settings are adaptable to be modified by a clinician or user if necessary depending on the progress of the negative pressure therapy and/or instillation therapy being applied.

In some example embodiments, a QR code may be encoded with a variety of initial therapy settings comprising a desired therapy configuration such as, for example, a list of therapy settings set forth in Table 1 which is not an exhaustive list of possible therapy settings. In some embodiments, the therapy settings may comprise three groups of therapy categories including negative pressure therapy, instillation therapy, and/or the scheduling of either one or both, each one comprising a plurality of possible setting descriptions. For example, the negative pressure category may comprise a plurality of setting descriptions including a name identifying the specific device, a target pressure (TP), and a therapy range (TR). The negative pressure category may also comprise an indication of the desired mode of operation, i.e., continuous pressure control (CPC), intermittent pressure control (IPC), and dynamic pressure control (DPC), and a cycle time for activating and deactivating the negative pressure therapy as described above with respect to FIGS. 2 and 3. Each mode of operation may include therapy settings peculiar to the specific mode of operation that is selected and stored on the QR code. For example, if the intermittent pressure control (IPC) is selected, the QR code may include the duty cycle therapy settings representing the ratio for the on-time and off-time for each cycle of the negative pressure therapy as described in more detail above. If the dynamic pressure control (DPC) is selected, the QR code may include the waveform of the desired pressure such as, for example, a triangular waveform and the corresponding maximum and minimum pressure values as described above.

In some embodiments, the instillation category may comprise a plurality of possible setting descriptions including, for example, the type of solution to be utilized, the fill volume, the dwell time, and the maximum fluid pressure, all of which are described above with respect to FIG. 4. The instillation category also may comprise therapy setting relating to the timing of instillation therapy being applied such as, for example, the frequency of doses in the ratio of number of negative pressure cycles to the number of instillation cycles.

Additionally, the scheduling category also may comprise a plurality of possible setting descriptions for both the negative pressure category and the instillation category including, for example, a desired ratio of the negative pressure cycles to the instillation cycle, a daily regimen for each therapy category, a weekday regimen for each therapy category and a weekend regimen for each therapy category. For example, a weekday regimen may include instillation therapy three times per day and a weekend regimen that includes no instillation therapy because clinicians may not be available over the weekend. In some embodiments, the daily regimen for instillation therapy may be set to decline over a week such as, for example, including instillation therapy five times for the first day of therapy, four times for the second day of instillation therapy, and three times for the third day which continues at that level for the remainder of the instillation cycle.

TABLE 1

Therapy Settings Template

| Therapy Categories | Setting Descriptions |
|---|---|
| Negative Pressure: | Device Name |
| | Target Pressure (TP) |
| | Therapy Range (TR) |
| | Mode: CPC/IPC/DPC |
| | Cycle Time |
| Instillation: | Solution Type |
| | Fill Volume |
| | Dwell Time |
| | Fluid Pressure |
| | Doses per day |
| | NP/IN Ratio |
| Scheduling: | Daily Regimen (NP/IN) |
| | Weekday Regimen (NP/IN) |
| | Weekend Regimen (NP/IN) |

FIG. 6A is an example embodiment of a QR code that stores an initial therapy template comprising some of the therapy settings for providing negative pressure and instillation therapy, and FIG. 6B is the information stored by the QR code. In this embodiment, the QR code is encoded as a machine-readable QR label 600 that contains information regarding the initial therapy values associated with a therapy device such as, for example, therapy device 101 that provides both negative pressure and instillation therapy, and utilizes a dressing suitable for such therapy. For example, the QR code 600 may be attached to the therapy device 101 and be encoded to identify the dressing (e.g., V.A.C. VERAFLO™ dressing described above). As indicated above, the QR code 600 may be attached to the therapy device 101 as a label or displayed by the LCD 508. In some embodiments, the QR label 600 may further identify the fill volume of fluids to be provided for each dose (e.g., 50 cc), the dwell time for allowing the fluid to soak into the dressing 102 (e.g., 30 seconds), the target pressure for a negative pressure therapy (e.g. 125 mmHg), and an intermittent pressure control (IPC) indicating the amount of time the negative pressure therapy is activated and deactivated, i.e., on time and off time (e.g., 3 minutes on and 10 minutes off).

As indicated above, the initial therapy template and the QR code 600 may be modified by a clinician or user to create a modified therapy template stored in a modified QR code if necessary depending on the progress of the negative pressure therapy and/or instillation therapy being applied. For example, the clinician may desire to switch to more aggressive therapy cycles prior to changing the dressing at the tissue site and may modify the therapy settings to increase both the instillation therapy cycle and the negative pressure therapy cycle. More specifically, the clinician may increase the dwell time therapy setting to 1 minute and the negative pressure cycle to 30 minutes for the last two instillation and negative pressure therapy cycles. In another example, the clinician may desire to switch to a lower instillation volume and a longer dwell time for weekend therapy to reduce the likelihood of generating a bag empty, canister full, or fluid leakage alarm condition as described in more detail below. In yet another example, the clinician may desire to switch to a higher target pressure (TP) to compensate for leaks in the therapy system 100 in order to reduce the likelihood of generating a fluid leakage alarm condition as also described in more detail below.

Figure 7:
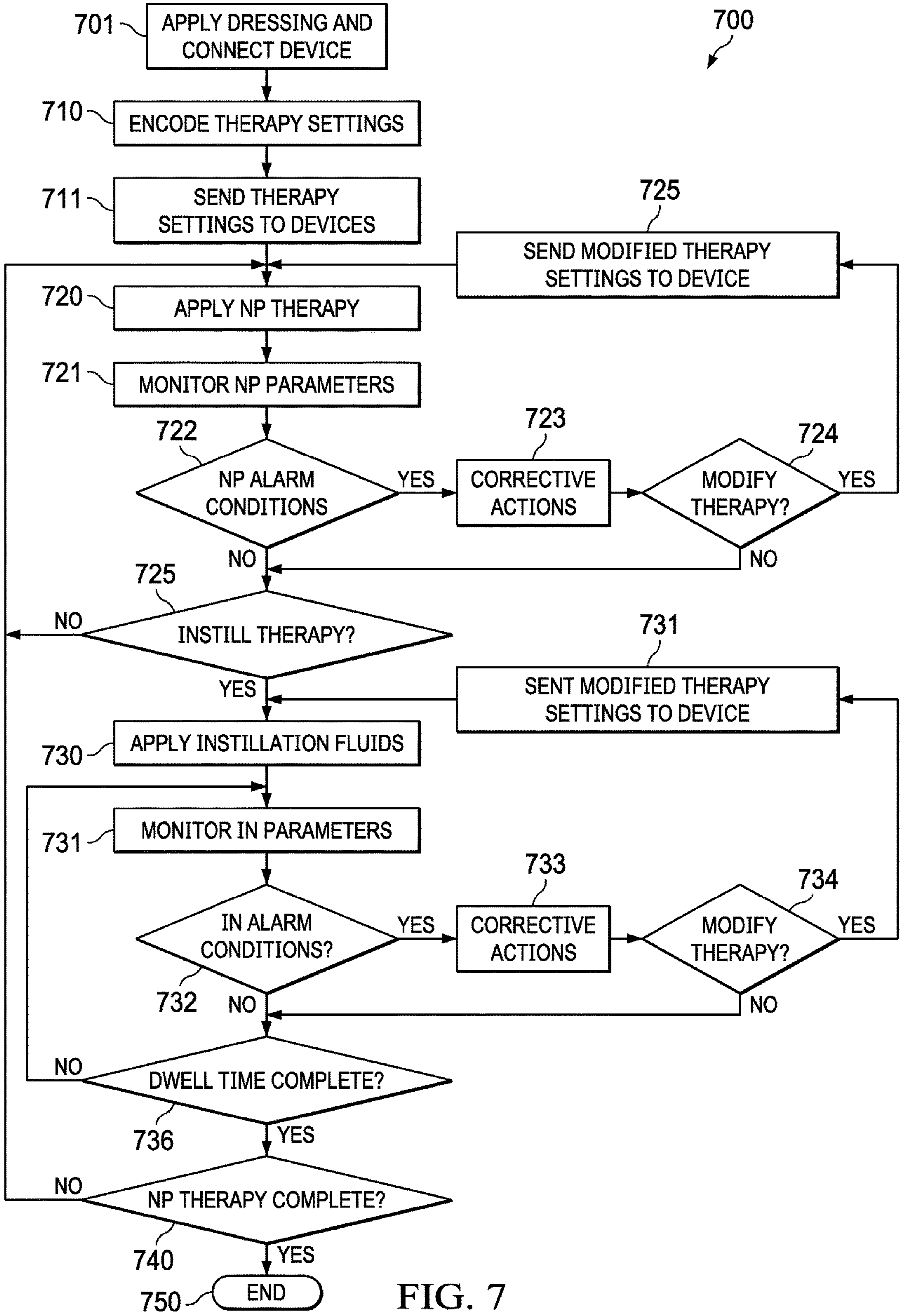
FIG. 7 is a flow chart illustrating a method for treating a tissue site utilizing a therapy configuration that may be associated with some embodiments of the therapy system of FIG. 1 and the QR code of FIG. 6A.

FIG. 7 is a flow chart illustrating a method 700 for treating a tissue site utilizing a therapy configuration that may be associated with some embodiments of the therapy system of FIG. 1, a method of operating the therapy system of FIG. 4, and the QR code of FIG. 6A. More specifically, such method may utilize a dressing such as, for example, the dressing 102 for applying negative-pressure therapy with fluid instillation therapy based on the therapy template described in connection with the Table 1. A dressing such as, for example, the dressing 102 may be applied to the tissue site, and connected to a therapy device such as, for example, therapy device 101 as indicated at 701. In some embodiments, therapy settings for a therapy configuration may be encoded such as, for example, the therapy settings for the therapy categories listed in Table 1 and, more specifically, the therapy settings associated with the QR code 600 as indicated at 710. The therapy settings may then be sent to the relevant therapy device and various remote devices, and/or be printed and forwarded to clinicians and nurses who are responsible for activating and monitoring the therapy as indicated at 711. In some embodiments, these therapy settings may be embodied in a QR code such as, for example, QR code 600 that may be loaded into the memory of the processor 503 of the therapy device 101. The QR code 600 may be loaded into the processor 503 by utilizing the reader 530 to read the therapy settings of the QR code or by utilizing a wireless version of the remote device 522 to transmit the QR code to the processor 503 read on the LCD 508.

Negative pressure therapy may then be applied by the therapy device to the dressing at 720 such as, for example, the therapy device 101 applying negative pressure to the dressing 102. As the therapy device draws down the pressure at the tissue site, the therapy device monitors the operating parameters associated with the application of negative pressure at 721. In some embodiments, the control sensor 120 and the supply sensor 124 monitor the control pressure and the supply pressure, respectively, to identify any negative pressure alarm conditions that may occur within the therapy system 100 such as, for example, leak conditions, blockage conditions, canister-full conditions, and/or over-pressure conditions. If a negative pressure alarm condition occurs, corrective action may be taken by the clinician or user at 723 and, in some example embodiments, the initial therapy settings of the therapy configuration may be modified by the clinician at 724. In some embodiments, the modified therapy configuration may be encoded and stored in a modified QR code so that the modified QR code may be sent to the therapy device 101 and other remote devices such as, for example, remote device 520, at 725 and the negative pressure therapy can continue at 720 utilizing the modified therapy settings of the modified therapy configuration.

In some example embodiments, the processor 503 may be configured to monitor the control sensor 504 and the supply sensor 514 to determine if the draw-down process is occurring within desired parameters such as, for example, the target pressure (TP) and the therapeutic range (TR). In some embodiments, the processor 503 may be configured to determine whether the control pressure determined by the control sensor 120 has reached the desired therapy pressure that may have been determined by setting the target pressure (TP) in the processor 503 at the desired therapy pressure. In such embodiments, the control pressure measured may be equal to the target pressure (TP). In some embodiments, the processor 503 may be configured to determine the difference between the control pressure determined by the control sensor 120 and a supply pressure determined by the supply sensor 124, and then store the pressure difference or pressure differential for display on the LCD 508 as a possible negative pressure alarm condition. In this manner, the processor 503 may signal an operating state of the system during the draw-down process.

In some embodiments, processor 503 and the therapy configuration embodied in the QR code 600 may be configured to identify a negative pressure leak condition. For example, if the control pressure is within the therapeutic range (TR) of the target pressure (TP), the processor 503 may be configured to continue the application of negative pressure therapy and continue monitoring the control pressure provided by the control sensor 120 and the supply pressure determined by the supply sensor 124 because no alarm condition has been identified. If the processor 503 determines that the control pressure exceeds the lower limit of the therapeutic pressure range (TR) and the supply pressure is within the therapeutic range of the target pressure (TP), then the processor 503 can provide an indication on the LCD 508 that a first type of leak condition has occurred. In this condition, the therapy system 100 may be leaking between the negative pressure source 104 and the control sensor 120. However, if both the control pressure and the supply pressure exceed the lower limit of the therapeutic range (TR), then the processor 503 can provide an indication on the LCD 508 that a second type of leak condition has occurred. In this condition, the negative pressure source 104 may also have a problem. In some embodiments, the processor 503 also may be configured to provide an output signal to the negative pressure source 104 that increases the supply pressure being provided by the pressure source 104 to compensate for the leak condition in the therapy system 100. In some other embodiments, the clinician or user may take a corrective action by attempting to find the leak in the therapy system 100 and fix or repair the leak. In yet other embodiments, the clinician or user may discover that the dressing 102 is leaking a little bit more than when initially applied to the tissue site, and decide to simply adjust the target pressure (TP) or the therapeutic range (TR). If the clinician decides to modify either one of these therapy settings, the modified therapy configuration may then be encoded and stored on a modified QR code so that the negative pressure therapy can continue at 710 utilizing the modified therapy settings.

In some embodiments, processor 503 and the therapy configuration embodied in the QR code 600 may be configured to identify a negative pressure blockage condition. For example, if the processor 503 determines that the control pressure provided by the control sensor 120 remains static while the supply pressure provided by the supply sensor 124 changes, such as an increase or decrease in pressure, the processor 503 can provide an indication on the LCD 508 or the remote device 520 that a blockage condition has occurred. For example, the supply sensor 120 may provide a signal indicating that the supply pressure exceeds the upper limit of the therapeutic range (TR). If the control sensor 124 provides a signal indicating that the control pressure remains within the therapeutic range (TR), the processor 503 can provide an indication on the LCD 508 and/or the remote device 120 that the operating state of the therapy system 100 is a blockage condition. In some embodiments, the processor 503 also may provide an output signal to the regulator valve 118 to close the valve in order to maintain the desired therapy pressure. In other embodiments, the processor 503 may provide an output signal to the negative pressure source 104 to decrease the supply pressure being provided by the negative pressure source 104 to identify the location of the blockage in the therapy system 100.

In some embodiments, processor 503 and the therapy configuration embodied in the QR code 600 may be configured to identify a negative pressure canister-full condition. For example, if the supply sensor 124 provides successive signals to the processor 503 that is configured to determine that the supply pressure is rising during a preset time at a rate that exceeds a preset rate tolerance, and the control sensor 120 provides a signal indicating that the control pressure remains static, the processor 503 can provide an indication on the LCD 508 or remote device 520 that a canister-full condition has occurred. In some embodiments, the processor 503 may provide an output signal to turn off the supply pressure being provided by the negative pressure source 104 so that the negative pressure therapy is temporarily disabled. In some embodiments, the system pressure remains disabled and the alarms continue, e.g., visual and/or audible, until the clinician takes corrective action to empty or replace the container 112. In other embodiments, the processor 503 also may be configured provide an output signal to the regulator valve 118 to vent the negative pressure from the system in order to equalize the pressure within the container 112 and returning the pressure to ambient pressure.

In some embodiments of the method 700, negative pressure therapy may continue to be applied to the tissue site and negative pressure alarm conditions may continue to be monitored until the negative pressure therapy is discontinued or installation therapy is selected at 725. As indicated above with respect to FIG. 4, instillation therapy may be provided indirectly to a tissue site by applying a negative pressure from the negative-pressure source 104 to the tissue site, thereby reducing the pressure at the tissue site and drawing solution from the solution source 114 into the tissue interface 108. Alternately, instillation therapy may be provided directly to a tissue site by applying a positive pressure from the positive-pressure source 116 to motivate solution from the solution source 114 to the tissue interface 108. The positive-pressure source 116 may be, for example, a peristaltic pump. Whether utilizing a negative pressure source or a positive-pressure source, the controller 110 may be configured to control the fluid dynamics of instillation therapy by providing a continuous flow of solution or an intermittent flow of solution. In this example embodiment, the method 700 may use a negative pressure source to provide an intermittent flow of solution for either instillation therapy or negative pressure therapy depending upon which therapy is being activated.

In some embodiments of the method 700, negative pressure therapy may continue until instillation therapy is activated at 725. For example, negative pressure therapy may be discontinued because a first cycle of negative pressure therapy has been completed or because the negative pressure therapy is preempted by the next cycle for instillation therapy. In some embodiments, the method 700 may engage a subroutine (not shown) indicating that the cycle time of negative pressure therapy had not expired and should continue to be applied at 720. In some embodiments, the processor 503 may be configured to discontinue the application of negative pressure and commenced instillation therapy at 730 based on the ratio of a negative pressure cycle to an instillation therapy cycle which can be identified as one of the therapy settings stored on the QR code 600. In yet other embodiments, a clinician or user may manually switch between negative pressure therapy and fluid instillation therapy.

Fluid instillation therapy may then be applied by the therapy device to the dressing at 730 such as, for example, the therapy device 101 may apply fluid instillation to the dressing 102. As the therapy device draws the instillation fluid into the dressing 102 at the tissue site, the therapy device 101 monitors the operating parameters associated with the application of instillation fluids at 731. In some embodiments, the control sensor 120 and the supply sensor 124 continue to monitor the control pressure and the supply pressure, respectively, to identify any instillation alarm conditions that may occur within the therapy system 100 such as, for example, fluid blockage conditions, bag empty condition, and/or total volume dispensed conditions. If a fluid instillation alarm condition occurs, corrective action may be taken by the clinician or user at 733 and, in some example embodiments, the initial therapy settings of the therapy configuration may be modified by the clinician at 734. In some embodiments, the modified therapy configuration may be encoded and stored in a modified QR code so that the modified QR code may be sent to the therapy device 101 and other remote devices such as, for example, remote device 520, at 735 and the fluid instillation therapy can continue at 730 still activated utilizing the modified therapy settings of the modified therapy configuration. It should be understood that one skilled in the art would know how to configure the controller 110 to compute the instillation alarm conditions depending on whether a negative-pressure source or a positive-pressure sores is used to provide the solution therapy.

In some embodiments, the processor 503 and the therapy configuration embodied in the QR code 600 may be configured to identify an instillation blockage condition and automatically switch from instillation therapy back to negative pressure therapy. In some embodiments, the supply sensor 120 may provide a signal indicating that the supply pressure exceeds the upper limit of the therapeutic range (TR). If the control sensor 124 provides a signal indicating that the control pressure remains within the therapeutic range (TR), the processor 503 can provide an indication on the LCD 508 and/or the remote device 120 that a blockage condition has occurred. In some embodiments, the processor 503 also may provide an output signal to the instillation regulator 115 to close the valve in order to turn off the instillation therapy. In other embodiments, the processor 503 may provide an output signal to the negative pressure source 104 to decrease the supply pressure being provided by the negative pressure source 104 to identify the location of the blockage in the therapy system 100. After corrective actions have been taken, the initial therapy template and the QR code 600 may be modified by a clinician or user to create a modified therapy template stored in a modified QR code. For example, the clinician may desire to switch to a lower instillation volume and a longer dwell time for weekend therapy to reduce the likelihood of generating a bag empty, canister full, or fluid leakage alarm condition.

In some embodiments, the processor 503 and the therapy configuration embodied in the QR code 600 may be configured to identify an instillation bag empty condition and automatically switch from instillation therapy back to negative pressure therapy. If the controller 110 provides a signal indicating that the solution source 114 is empty, the processor 503 can provide an indication on the LCD 508 and/or the remote device 120 that a bag empty condition has occurred. In some embodiments, the processor 503 also may provide an output signal to the instillation regulator 115 to close the valve in order to turn off the instillation therapy. In some other embodiments, the processor 503 also may provide an output signal to start a dwell time clock (not shown) that times out after the dressing has soaked for the dwell time embodied in the QR code 600. If the dwell time has not expired at 736, the method 700 continues to monitor the instillation parameters at 731 to detect any instillation alarm conditions at 732. However, if the dwell time has expired at 736, the method 700 may proceed to 740 to determine whether the negative pressure therapy has been completed. If negative pressure therapy has not been completed at 740, the method 700 may proceed back to 720 to apply another cycle of negative pressure therapy. However, if the negative pressure at 740 has been completed, therapy treatments may be completed at 750.

The systems, apparatuses, and methods described herein may provide significant advantages. For example, throughout the application of various therapy configurations including both negative pressure therapy and instillation therapy, the therapy device applying the therapy may generate a large number of alarms as a result of alarm conditions described above for different therapy settings. The systems, apparatuses, and methods described herein may allow the supplier of the therapy device or therapy disposables, the clinician or the user to identify various therapy configurations embodied in and initial therapy template that may be easily modified by the clinician or user to generate a modified therapy configuration to facilitate the reduction of alarms when applying the therapy. The initial therapy configuration and the modified therapy configuration may be stored on the respective therapy template in a readable code such as, for example, a QR code to further facilitate the clinician or user's ability to control the number of alarms generated by the therapy device during the therapy treatment.

The systems, apparatuses, and methods described herein may also allow the clinician to utilize in initial therapy template to initiate therapy in a consistent and easy-to-use manner because the template may include predefined therapy settings for both negative pressure therapy (e.g., target pressure, intermittent or dynamic pressure control, etc.) and instillation therapy (e.g., fill volume, dwell time, etc.). A supplier of a therapy device and/or therapy disposables may provide guidelines and/or algorithms to users and/or clinicians for selecting the recommended therapy settings for an initial therapy template to initiate the therapy. These initial therapy settings may be customized for specific care groups, hospitals, or care facilities. The therapy settings may be further modified in light of various clinical parameters such as the type of wound or incision, clinical intervention, or other parameters unique to the patient and/or treatment being provided. Additionally, the therapy configurations comprising the therapy settings may be encoded and stored in a standard barcode or a standard QR code as described above, and the code may be stored on a therapy device or package label to further facilitate customization and or modification of the therapy configuration to better control or limit the number of alarm conditions that may occur. Such codes may be scanned by a reader to display the current therapy configuration being applied or utilized. Such codes may also be transferred to the therapy device via wire or wireless connections such as, for example, USB or Bluetooth connections, respectively.

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing 110, the container 115, or both may be eliminated or separated from other components for manufacture or sale. In other example configurations, the controller 110 may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims.

What is claimed is:

1. A method for controlling and monitoring a negative-pressure wound treatment device, the method comprising:

transferring an initial therapy configuration from a code that is machine readable to a processor of a therapy device, wherein the therapy device comprises a source of negative pressure, a source of instillation fluid, and a controller including the processor, and wherein the initial therapy configuration includes instillation therapy;

controlling, using the controller, the source of instillation fluid to supply instillation fluid to a dressing based on the initial therapy configuration;

monitoring, at the controller, instillation parameters associated with the supplying of instillation fluid to the dressing to identify instillation alarm conditions;

providing a first corrective action in response to identification of an instillation alarm condition, wherein the first corrective action includes stopping the instillation therapy and starting negative pressure therapy;

controlling, using the controller, the source of negative pressure to apply a first therapeutic negative pressure to a dressing based on the initial therapy configuration;

monitoring, at the controller, negative pressure parameters associated with the application of negative pressure to the dressing to identify negative pressure alarm conditions; and providing a second corrective action in response to identification of a negative pressure alarm condition, the second corrective action being an adjustment to the source of negative pressure of the negative-pressure wound treatment device made automatically by the controller, wherein the negative pressure alarm condition is a leak condition and the second corrective action is increasing the negative pressure being applied to the dressing from the first therapeutic negative pressure to a second therapeutic negative pressure.

2. The method of claim 1, wherein a further negative pressure alarm condition is a blockage condition and the second corrective action is turning off the application of negative pressure being applied to the dressing.

3. The method of claim 1, wherein the instillation alarm condition is a bag empty condition and the first corrective action includes turning off the supply of the instillation fluid being applied to the dressing before starting the negative pressure therapy.

4. The method of claim 3, further comprising allowing the instillation fluid to soak the dressing for a dwell time before starting the negative pressure therapy.

5. The method of claim 1, wherein the initial therapy configuration comprises therapy settings selected from a group of negative pressure therapy settings including identification of a therapy device, a target pressure, a therapeutic range, a pressure control mode, and a cycle time.

6. The method of claim 1, wherein the initial therapy configuration comprises therapy settings selected from a group of instillation therapy settings including identification of an instillation fluid, a fill volume, a dwell time, a fluid pressure, and a negative pressure/instillation ratio.

7. The method of claim 1, wherein the initial therapy configuration comprises therapy settings selected from a group of scheduling therapy settings including a daily regimen, a weekday regimen, and a weekend regimen for applying negative pressure and instillation fluid.

8. The method of claim 1, wherein the code is adaptable to be modified.

9. The method of claim 1, further comprising storing the code on the therapy device.

10. The method of claim 1, further comprising printing the code on a label associated with the therapy device or a package associated with disposals used with the therapy device.

11. The method of claim 1, wherein transferring the code with the initial therapy configuration to the therapy device is completed from a wireless mobile device.

12. The method of claim 1, wherein the code is attached to the therapy device.

13. The method of claim 1, wherein the code that is machine readable is a barcode or a QR code and the initial therapy configuration is retrieved from the code by scanning the code with a reader and transferring the initial therapy configuration from the reader to the processor of the therapy device.

14. The method of claim 1, further comprising:

modifying, using the controller, the initial therapy configuration to generate a first modified therapy configuration in response to identification of the negative pressure alarm conditions.

15. The method of claim 14, wherein providing the second corrective action in response to identification of the negative pressure alarm conditions occurs prior to modifying the initial therapy configuration.

16. The method of claim 14, wherein modifying the initial therapy configuration results from an input from a clinician.

17. The method of claim 14, wherein modifying the initial therapy configuration results from an alarm condition.

18. The method of claim 14, further comprising:

storing the first modified therapy configuration on a first modified code that is machine-readable, the first modified code being a first modified barcode or a first modified QR code.

19. The method of claim 1, further comprising:

modifying, using the controller, the initial therapy configuration to generate a second modified therapy configuration in response to identification of the instillation alarm conditions; and storing the second modified therapy configuration on a second modified code that is machine-readable, the second modified code being a second modified barcode or a second modified QR code.

20. The method of claim 19, wherein providing the first corrective action in response to identification of the instillation alarm conditions occurs prior to modifying the initial therapy configuration.

* * * * *